US00PP26737P3

(12) United States Plant Patent

Klemm et al.

(10) Patent No.: US PP26,737 P3

(45) Date of Patent: May 17, 2016

(54) *CALCEOLARIA* PLANT NAMED 'KLECH13020'

(50) Latin Name: *Calceolaria hybrida*
Varietal Denomination: KLECH13020

(71) Applicant: Klemm+Sohn GmbH & Co. KG, Stuttgart (DE)

(72) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 142 days.

(21) Appl. No.: 14/120,149

(22) Filed: Apr. 30, 2014

(65) Prior Publication Data

US 2015/0319903 P1 Nov. 5, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Keith Robinson
(74) *Attorney, Agent, or Firm* — James M. Weatherly; Bethany R. Roahrig; Cochran Freund & Young, LLC

(57) ABSTRACT

A new *Calceolaria* plant particularly distinguished by having a red-black flower color, a red-black upper lip (hood) with a yellow border, and a stretching plant habit, is disclosed.

1 Drawing Sheet

Genus and species: *Calceolaria hybrida.*
Variety denomination: 'KLECH13020'.

BACKGROUND OF THE NEW PLANT

The present invention comprises a new and distinct variety of *Calceolaria*, botanically known as *Calceolaria hybrida* and hereinafter referred to by the variety name 'KLECH13020'. 'KLECH13020' is a selection from a cross-pollination of the proprietary female *Calceolaria* line 'CH-2008-0199' (unpatented) and the proprietary male *Calceolaria* line 'CH-2008-0198' (unpatented).

In June of 2008 the proprietary female *Calceolaria* line 'CH-2008-0199' and the proprietary male *Calceolaria* line 'CH-2008-0198' were cross pollinated in Stuttgart, Germany and seeds were obtained. The seeds were sown in the winter of early 2009 and grown in a greenhouse after crop specific cultivation selection was done. A plant line was selected in Stuttgart, Germany in May of 2009 and named 'KLECH13020'. First cuttings of 'KLECH13020' were taken in June 2009 in Stuttgart, Germany to build up an elite stock and has been propagated six times by cuttings. 'KLECH13020' was found to reproduce true to type in successive generations of asexual propagation via stem cuttings in Stuttgart, Germany.

CROSS REFERENCE TO RELATED APPLICATIONS

Plant Breeder's Rights for 'KLECH13020' were applied for in Canada on Feb. 3, 2014 (14-8193). 'KLECH13020' has not been made publicly available or sold more than one year prior to the filing date of this application.

SUMMARY

The following are the most outstanding and distinguishing characteristics of this new variety when grown under normal horticultural practices in Stuttgart, Germany.

1. Red-black flower color;
2. A red-black upper lip (hood) with a yellow border; and
3. A stretching plant habit.

DESCRIPTION OF THE PHOTOGRAPH

This new *Calceolaria* plant is illustrated by the accompanying photograph which shows an overall view of the plant. The plant is about 3 months-old grown indoors in Stuttgart, Germany in April 2013. The colors shown are as true as can be reasonably obtained by conventional photographic procedures.

DESCRIPTION OF THE NEW VARIETY

The following detailed descriptions set forth the distinctive characteristics of 'KLECH13020'. The data which define these characteristics were collected from asexual reproductions carried out in Stuttgart, Germany. Data was collected on three-month-old plants grown indoors in Stuttgart, Germany under greenhouse conditions in April of 2013. Color references are to The R.H.S. Colour Chart of The Royal Horticultural Society of London (R.H.S.), 5$^{th}$ edition (2007).

Classification:
- *Family.*—Calceolariaceae.
- *Species.*—*Calceolaria hybrida.*
- *Common name.*—Lady's purse, slipper flower, pocket-book flower.
- *Variety.*—'KLECH13020'.

Parentage:
- *Female.*—Proprietary *Calceolaria* line 'CH-2008-0199'.
- *Male.*—Proprietary *Calceolaria* line 'CH-2008-0198'.

Plant:
- *Form.*—Potted plant.
- *Habit.*—Upright.
- *Plant height.*—Approximately 27.0 cm.
- *Plant width.*—Approximately 33.0 cm.

*Flowering habit.*—Continuous, but intermittent in summertime.

*Time to produce a finished flowering plant.*—10 to 11 weeks (in 12 cm pot).

*Propagation type.*—Stem cuttings.

*Time to initiate roots.*—5 to 6 weeks.

*Root description.*—Adventitious, fibrous root system, with fine light brown roots, RHS 164C.

Stems:

*Quantity per plant.*—5 to 8.

*Color.*—RHS 187A, then with maturity getting lighter and greener to RHS 142B.

*Length.*—Approximately 6.0 cm.

*Diameter.*—Approximately 0.5 cm.

*Internode length.*—Approximately 2.5 cm.

*Texture.*—Less pubescent, hairs are very small and soft, not sticky.

*Anthocyanin.*—Present, RHS 187A.

Leaves:

*Arrangement.*—Decussate.

*Length.*—2.0 cm (small, younger leaves); 9.5 cm (bigger, old leaves).

*Width.*—1.0 cm (small, younger leaves); 7.5 cm (bigger, old leaves).

*Shape.*—Rhombical.

*Apex.*—Obtuse.

*Base.*—Attenuate.

*Margin.*—Crenate.

*Texture.*—Upper surface: Leathery and smooth. Lower surface: Very fine hairs.

*Glossiness.*—Weak.

*Variegation.*—Absent.

*Color.*—Immature leaf: Upper surface: RHS 137B to 137A. Lower surface: RHS 137D. Mature leaf: Upper surface: RHS 137B to 137A. Lower surface: RHS 137D.

*Venation pattern.*—reticulate.

*Venation color.*—Upper surface: RHS 137D. Lower surface: RHS 137D.

*Petiole.*—Length: Approximately 1.0 cm. Diameter: 0.5 cm to 1.5 cm. Color: RHS 137D with anthocyanin RHS 187A. Texture: Pubescent, but hairs are very small and not sticky.

Flowers:

*General.*—Zygomorphic with a four-parted calyx, with the lobes free to the base, and a two-lipped sympetalous corolla.

*Flowering season.*—Without artificial light, from May to June and August to October.

*Lastingness of individual flowers on the plant.*—About 3 weeks.

*Fragrance.*—Absent.

Bud:

*Shape.*—Truncate hemisphere.

*Height.*—About 0.4 cm.

*Width.*—0.6 cm to 1.5 cm.

*Color.*—RHS 187B.

*Texture.*—Velvety, not pubescent.

Corolla:

*General.*—The corolla is two-lipped and composed of two pouches, the upper lip and the lower lip.

*Flower length.*—Approximately 3.5 cm.

*Flower width.*—Approximately 3.0 cm.

*Upper lip.*—Hood: Present, RHS 187B with light yellow border RHS 4D. Length: Approximately 1.2 cm. Width: Approximately 0.3 cm. Texture: Velvety, not pubescent. Color: Immature: RHS 187A. Mature: RHS 187A changing to lighter RHS 187B with maturity. Shape: Hemispherical. Apex: Elliptical. Base: Fused with the lower lip more flattened. Margin: Entire.

*Lower lip.*—Length: Approximately 2.3 cm. Width: Approximately 2.6 cm. Texture: Velvety, not pubescent. Color: Immature: RHS 187A. Mature: RHS 187B. Shape: Hemispherical. Apex: Elliptical. Base: Fused with upper lip more flattened. Margin: Entire. Oil gland: Absent.

Calyx: Four-parted calyx; all calyx lobes showing similar size.

*Sepals.*—Upper Sepal: Length: Approximately 0.5 cm. Width: Approximately 0.6 cm. Color: Upper surface: RHS 137C. Lower surface: RHS 137D with anthocyanin RHS 187A. Texture: Leathery. Shape: Ovate (egg shape) with acuminate sepal tip. Apex: Acuminate. Base: Fused with three other sepals. Margin: Entire. Lateral sepals: Length: Approximately 0.5 cm. Width: Approximately 0.6 cm. Color: Upper surface: RHS 137C. Lower surface: RHS 137D with anthocyanin RHS 187A. Texture: Leathery. Shape: Ovate with acuminate sepal tip. Apex: Acuminate. Base: Fused with other sepals. Margin: Entire.

*Pedicel.*—Length: Approximately 1.5 cm. Diameter: Approximately 0.1 cm. Color: RHS 137D with anthocyanin RHS 187C. Texture: Smooth.

*Peduncle.*—Length: 3.0 cm to 10.0 cm. Diameter: Approximately 0.3 cm. Color: RHS 144D. Texture: Pubescent, sticky.

Reproductive organs:

*Stamens.*—Quantity per flower: 2. Filament length: Approximately 0.3 cm. Filament diameter: Approximately 0.1 cm. Filament Color: RHS 1D. Anther shape: Elliptic (Theca). Anther length: 0.2 cm (length of connective — Theca approximately 0.2 cm). Shape: Elliptic. Diameter: 0.1 cm. Anther color: RHS 4D. Pollen amount: Scarce. Pollen color: RHS 4D.

*Pistils.*—Quantity per flower: 1. Pistil length: Approximately 0.2 cm. Style length: Approximately 0.3 cm. Style color: RHS 187A. Stigma shape: Tube-like. Stigma color: RHS 4D. Ovary shape: Cylindrical. Ovary color: RHS 187B.

Fruit and seed set: After pollination, cark capsulates are developed. They are ovate-shaped, seeds are brown-black (RHS 200A), oblong to elliptic.

Disease and insect resistance: No particular disease or insect resistance observed.

COMPARISON WITH PARENTAL LINES AND KNOWN VARIETY

'KLECH13020' is a distinct variety of *Calceolaria*. 'KLECH13020' is distinguished from its parents as described in Table 1:

TABLE 1

| Comparison with Parental Lines | | | |
|---|---|---|---|
| Trait or characteristic | Variety 'KLECH13020' | Female parent 'CH-2008-0199' | Male Parent 'CH-2008-0198' |
| Habit | Stretching | Stretching | Not stretching |
| Flower color | Red-black | Red-black | Dark red |
| Flower size | Medium | Small | Medium |

'KLECH13020' is most similar to the commercial *Calceolaria* plant named 'Calynopsis Red' (unpatented). Differences between the two varieties are described in Table 2:

TABLE 2

| Comparison with Similar Variety | | |
|---|---|---|
| Trait or characteristic | Instant variety 'KLECH13020' | Commercial line: 'Calynopsis Red' |
| Flower color | Red-black | Red |
| Plant habit | Stretching | Not stretching |
| Upper lip (hood) | Red-black/light yellow border | Yellow |

We claim:

1. A new and distinct variety of *Calceolaria* plant named 'KLECH13020' as illustrated and described herein.

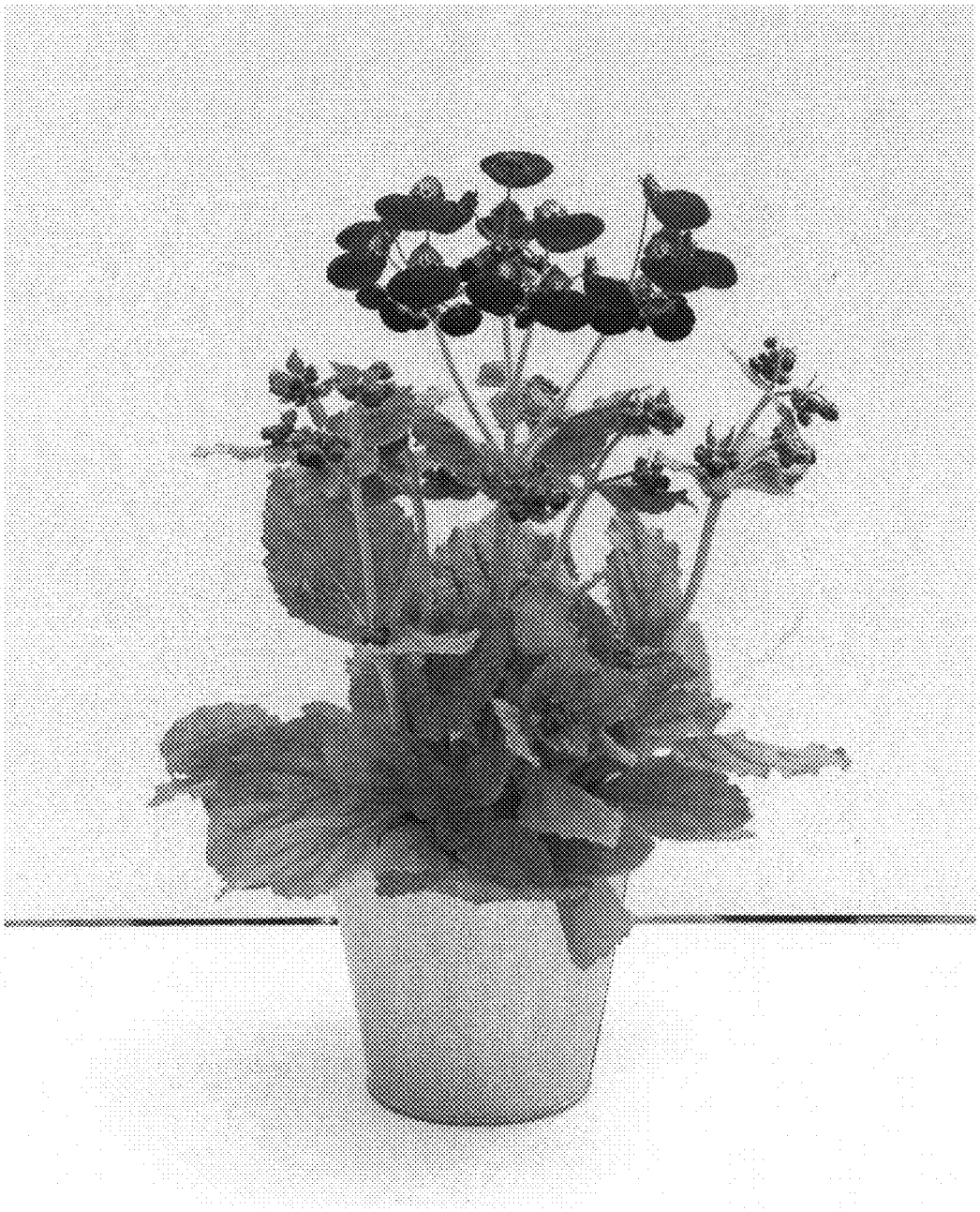

* * * * *